(12) United States Patent
Jadav et al.

(10) Patent No.: US 7,208,613 B2
(45) Date of Patent: Apr. 24, 2007

(54) SYNTHESIS OF S-FLUOROMETHYL 6α,9α-DIFLUORO-11β-HYDROXY-16α-METHYL-17α-PROPIONYLOXY-3-OXOANDROSTA-1,4-DIENE-17β-CARBOTHIOATE

(75) Inventors: Kanaksinh Jesingbhai Jadav, Baroda (IN); Sudhakar Kambhampati, Baroda (IN); Trinadha Rao Chitturi, Baroda (IN); Rajamannar Thennati, Baroda (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 311 days.

(21) Appl. No.: 10/517,944

(22) PCT Filed: Jun. 16, 2003

(86) PCT No.: PCT/IN03/00219

§ 371 (c)(1),
(2), (4) Date: Dec. 13, 2004

(87) PCT Pub. No.: WO04/001369

PCT Pub. Date: Dec. 31, 2003

(65) Prior Publication Data
US 2005/0256325 A1    Nov. 17, 2005

(30) Foreign Application Priority Data
Jun. 20, 2002    (IN)    .................. 544/MUM/2002
Apr. 17, 2003    (IN)    .................. 387/MUM/2003

(51) Int. Cl.
*C07J 3/00*    (2006.01)
(52) U.S. Cl. ...................................................... 552/610
(58) Field of Classification Search .................. 552/610
See application file for complete search history.

(56) References Cited

U.S. PATENT DOCUMENTS 4,335,121 A    6/1982    Phillipps et al.

FOREIGN PATENT DOCUMENTS

| GB | 2 088 877 A | 6/1982 |
| IL | 109656 | 2/1998 |
| WO | 01/62722 A2 | 8/2001 |

OTHER PUBLICATIONS

Gordon H. Phillipps et al, Journal of Medicinal Chemistry 37, 3717-3729 (1994).

*Primary Examiner*—Barbara P. Badio
(74) *Attorney, Agent, or Firm*—Merchant & Gould P.C.

(57) ABSTRACT

The present invention provides a convenient process for the preparation of S-fluoromethyl 6α,9α-difluoro-11β-hydroxy-16α-methyl-17α-propionyloxy-3-oxoandrosta-1,4-diene-17β-carbothioate, a compound of formula 1, comprising
(a) treating 17β-[(N,N-dimethylcarbamoyl)thio]carbonyl-6α,9α-difluoro-11β-hydroxy-16α-methyl-17α-propionyloxy-3-oxoandrosta-1,4-diene, a compound of formula 3 with alkali metal carbonate-alcohol system to obtain 6α,9α-difluoro-11β-hydroxy-16α-methyl-17α-propionyloxy-3-oxoandrosta-1,4-diene-17β-carbothioic acid, a compound of formula 4;
(b) reacting the compound of formula 4 with bromofluoromethane to yield the compound of formula 1.

19 Claims, No Drawings

SYNTHESIS OF S-FLUOROMETHYL 6α,9α-DIFLUORO-11β-HYDROXY-16α-METHYL-17α-PROPIONYLOXY-3-OXOANDROSTA-1,4-DIENE-17β-CARBOTHIOATE

The present invention relates to a convenient process for the preparation of S-fluoromethyl 6α,9α-difluoro-11β-hydroxy-16α-methyl-17α-propionyloxy-3-oxoandrosta-1,4-diene-17β-carbothioate, a compound of formula 1. S-fluoromethyl 6α,9α-difluoro-11β-hydroxy-16α-methyl-17α-propionyloxy-3-oxoandrosta-1,4-diene-17β-carbothioate, commonly known a fluticasone propionate (INN), is used as an anti-inflammatory and antipruritic agent.

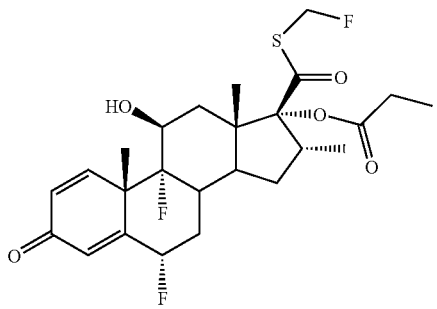

1

PRIOR ART

U.S. Pat. No. 4,335,121 (referred to herein as the '121 patent) discloses the compound of formula 1 and its preparation. It discloses the process of its preparation by treating 6α,9α-difluoro-11β-hydroxy-16α-methyl-3-oxo-17α-(propionyloxy) androsta-1,4-dien-17β-carboxylic acid, a compound of formula 2 with dimethylthiocarbamoyl chloride to yield 17β-[(N,N-dimethylcarbamoyl)thio]carbonyl-6α,9α-difluoro-11β-hydroxy-16α-methyl-17α-propionyloxy-3-oxoandrosta-1,4-diene, a compound of formula 3,

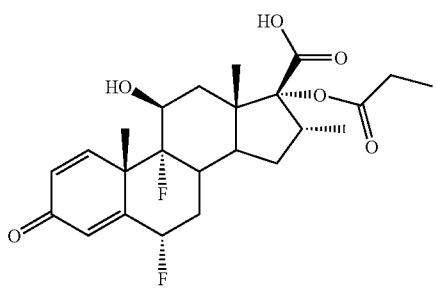

2

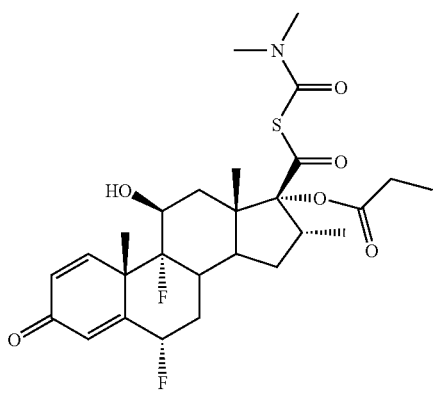

3

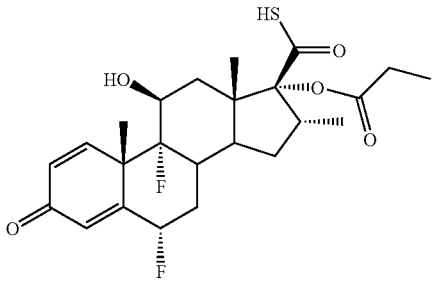

4

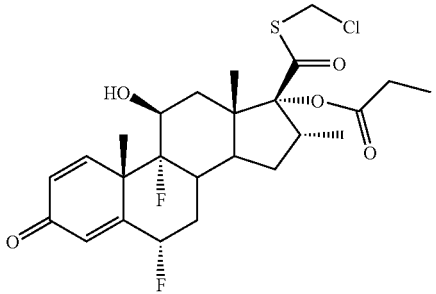

5 which is decomposed by refluxing in diethylamine to the thioic acid of formula 4. The compound of formula 4 is then reacted with bromochloromethane in presence of sodium bicarbonate to give a chloromethyl ester of formula 5. The compound of formula 5, is converted to an iodomethyl ester by halogen exchange and subsequently treated with silver fluoride to yield the compound of formula 1. This process of preparation of the compound of formula 1 is very tedious, lengthy, and involves use of expensive and sensitive chemicals, viz. silver fluoride. This prior art teaches the use of ammonia, a primary amine or more preferably a secondary amine such as diethylamine or pyrrolidine for conversion of compound of formula 3 to compound of formula 4. However, the yield obtained with use of secondary amines such as diethylamine is poor.

PCT publication WO 01/62722 (equivalent of which is U.S. 2002/0133032A1) discloses the method of preparing the compound of formula 1 by reacting a compound of formula 2 with dimethylthiocarbamoyl chloride and molar equivalents of sodium iodide in 2-butanaone to get compound of formula 3. The compound of formula 3 is then reacted with a hydrolyzing agent such as sodium hydrosulfide to generate the sodium salt of formula 4, which can be alkylated in-situ with chlorofluoromethane to yield the compound of formula 1 or alternately can be acidified to obtain the compound of formula 4, which can be isolated and converted to compound of formula 1 by alkylation with chlorofluoromethane. This prior art publication teaches the use of an alkoxide salt, a thioalkoxide salt or a hydrated sulfide salt for hydrolyzing the compound of formula 3 to obtain the corresponding thiocarboxylic acid, the compound of formula 4. The use of sodium hydrosulfide hydrate or sodium thiomethoxide as hydrolyzing agent for conversion of 17β-carboxylic acid to 17β-carbothioic acid, via the intermediacy of 17β-[(N,N-dimethylcarbamoyl)thio]carbonyl derivative, has been exemplified. However, sodium thiomethoxide is a corrosive and moisture sensitive reagent and use of sodium thiomethoxide would generate toxic methyl mercaptan during acidification and sodium hydrosulfide is unstable and converts to sodium thiosulfate and sodium carbonate upon storage. In the in-situ alkylation of sodium salt of compound of formula 4, the excess sodium hydrosulfide would react with the chlorofluoromethane generating toxic and obnoxious organosulfur byproducts, which can pose health hazards. Although isolation of thioic acid of formula 4 can be performed (by treatment with an acid) to overcome the problem, the excess sodium hydrosulfide would generate toxic hydrogen sulfide. Further, the thiosulfate impurity which is invariably present in sodium hydrosulfide, would generate sulfur upon acidification, which would contaminate the thioic acid and whose removal would poses difficulties.

Some other shortcomings of this prior art method include (i) the long reaction time required for the alkylation reaction with chlorofluoromethane, about 22 hours. (ii) large molar excess of chlorofluoromethane, requiring almost 7.5 molar equivalents, and (iii) handling difficulties with chlorofluoromethane, it being a gas. In contrast in the process of the present invention the reaction of thioic acid of formula 4 is carried out using only 1.28 equivalents of bromofluromethane, which is a liquid compound at below 15° C., for a period of about 2 hours only.

Gordon H. Phillipps et al, Journal of Medicinal Chemistry 37, 3717–3729 (1994), disclose the method of preparing the compound of formula 1 by treating a compound of formula 6 with carbonyldiimidazole under nitrogen, followed by a reaction with hydrogen sulfide to give the thioic acid of formula 7, which is isolated and treated with propionyl chloride to give the compound of formula 4. This compound is then alkylated with bromofluoromethane under nitrogen to yield the compound of formula 1 in 69.3% yield. This reference does not mention the preparation of compound of formula 1 directly from the compound of formula 3.

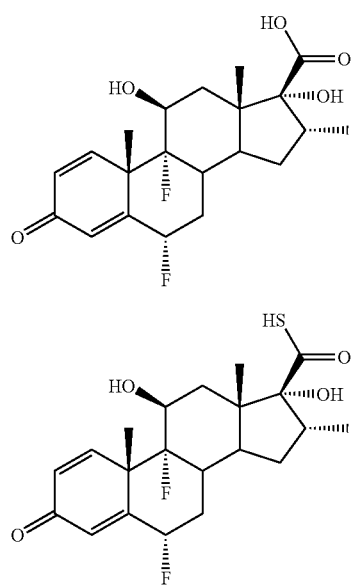

6

7

IL Patent No. 109656 discloses preparation of fluticasone propionate by esterification of compound of formula 4 with a halofluromethane, optionally in the presence of a catalyst such as tetrabutylammonium bromide.

In one aspect the present invention provides a convenient process for preparation of compound of formula 1, wherein an alkali metal carbonate-alcohol system is used for the conversion of 17β-[(N,N-dimethylcarbamoyl)thio]carbonyl-6α,9α-difluoro-11β-hydroxy-16α-methyl-17α-propionyloxy-3-oxoandrosta-1,4-diene, a compound of formula 3 to 6α,9α-difluoro-11β-hydroxy-16α-methyl-17α-propionyloxy-3-oxoandrosta-1,4-diene-17β-carbothioic acid, a compound of formula 4 in contrast to prior art use of an alkoxide, a thioalkoxide or hydrated sulphide salt (as in WO 01/62722) or use of amines such as diethylamine as in the '121 patent for this reaction.

In another aspect the present invention provides an improved process for preparation of compound of formula 1, wherein the compound of formula 2 is treated with N,N-dimethylthiocarbamoyl chloride in an inert aprotic solvent to obtain compound of formula 3, which is reacted with a hydrosulfide reagent and bromofluoromethane to obtain compound of formula 1. The advantages include an improved yield, use of reagents that are easy to handle, low reaction time and use of lesser molar amounts of the reagents.

OBJECT OF THE INVENTION

The object of the present invention is to provide a facile, efficient and economic process for the preparation of S-fluoromethyl 6α,9α-difluoro-11β-hydroxy-16α-methyl-17α-propionyloxy-3-oxoandrosta-1,4-diene-17β-carbothioate.

In particular, the process of the present invention provides a simple and economical process wherein an alkali metal carbonate-alcohol system is used for conversion of a compound of formula 3 to a compound of formula 4. Use of alkali metal carbonate-alcohol system provides improved yield of the compound of formula 4, without contamination by sulfur or other sulfur containing byproducts.

The present invention also provides an improved process for preparation of compound of formula 1, wherein the compound of formula 2 is treated with N,N-dimethylthiocarbamoyl chloride in an inert aprotic solvent to obtain compound of formula 3, which is reacted with a hydrosulfide reagent and bromofluoromethane to obtain compound of formula 1. The advantages include an improved yield, use of reagents that are easy to handle, low reaction time and use of lesser molar amounts of the reagents.

SUMMARY OF INVENTION

We have found a facile, efficient and economic process for the preparation of S-fluoromethyl 6α,9α-difluoro-11β-hydroxy-16α-methyl-17α-propionyloxy-3-oxoandrosta-1,4-diene-17β-carbothioate (compound of formula 1) that provides an improved yield of the compound, using reagents that are easy to handle, utilizing a low reaction time and using the reagents in lesser molar amounts.

In one aspect the present invention provides a process for the preparation of S-fluoromethyl 6α,9α-difluoro-11β-hydroxy-16α-methyl-17α-propionyloxy-3-oxoandrosta-1,4-diene-17β-carbothioate, a compound of formula 1, comprising
(a) treating the compound of formula 3 with an alkali metal carbonate-alcohol system to obtain the compound of formula 4;
(b) reacting the compound of formula 4 with bromofluoromethane to obtain the compound of formula 1.

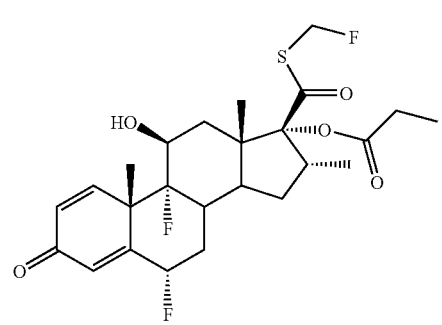

1

-continued

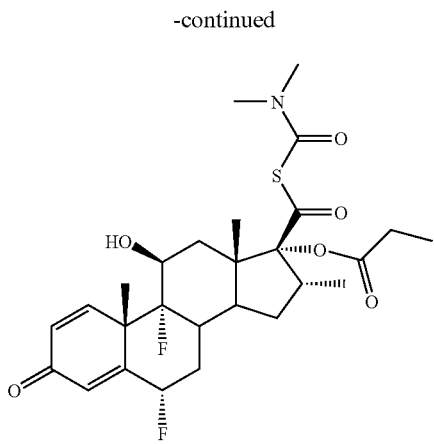

3

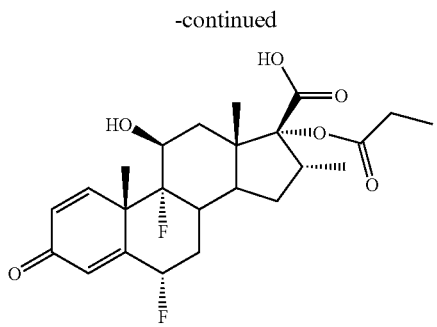

2

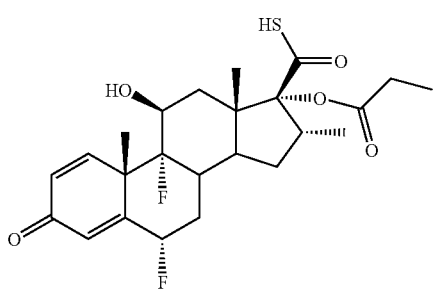

4

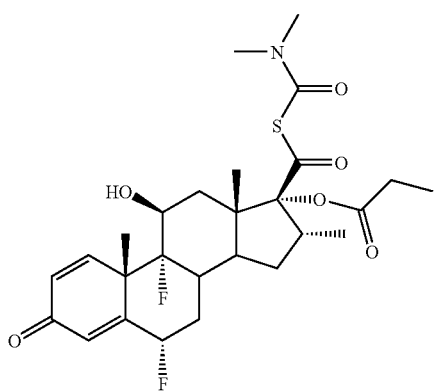

3

In another aspect the present invention provides an improved process for the preparation of S-fluoromethyl 6α,9α-difluoro-11β-hydroxy-16α-methyl-17α-propionyloxy-3-oxoandrosta-1,4-diene-17β-carbothioate, a compound of formula 1, comprising (a) reacting 6α,9α-difluoro-11β-hydroxy-16α-methyl-17α-propionyloxy-3-oxoandrosta-1,4-dien-17β-carboxylic acid, a compound of formula 2, with N,N-dimethylthiocarbamoyl chloride in an inert aprotic solvent in the presence of an iodide catalyst and a base to give a compound of formula 3, (b) reacting the compound of formula 3 with a hydrosulfide reagent and bromofluromethane to obtain a compound of formula 1.

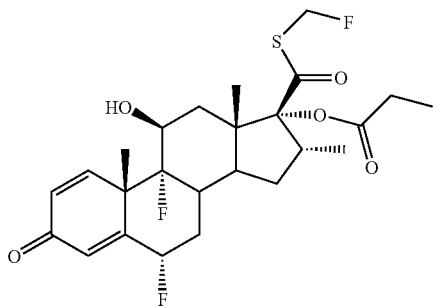

1

DETAILED DESCRIPTION OF THE INVENTION

The present invention provides a process for the preparation of S-fluoromethyl 6α,9α-difluoro-11β-hydroxy-16α-methyl-17α-propionyloxy-3-oxoandrosta-1,4-diene-17β-carbothioate, a compound of formula 1, comprising (a) treating the compound of formula 3 with an alkali metal carbonate-alcohol system to obtain the compound of formula 4;

(b) reacting the compound of formula 4 with bromofluoromethane to obtain the compound of formula 1.

In the process of the present invention the compound of formula 3 is converted to a compound of formula 4 by treating with alkali metal carbonate-alcohol system to generate the alkali metal salt of compound of formula 4, viz., a compound of formula 4a, wherein M is the metal ion corresponding to the alkali metal carbonate used, such as K, Na or Li. The compound of formula 4a can be neutralized in-situ by treatment with an acid to obtain the compound of formula 4. The compound of formula 4 is then reacted with bromofluoromethane to obtain the compound of formula 1. It is also possible to convert the compound of formula 3 to the compound of formula 1 directly in a one pot synthesis i.e. without isolating the compound of formula 4 by avoiding the reaction of compound of formula 4a with the acid, and directly reacting the compound of formula 4a generated in-situ with bromofluoromethane to obtain the compound of formula 1 (See Scheme 1).

Scheme 1

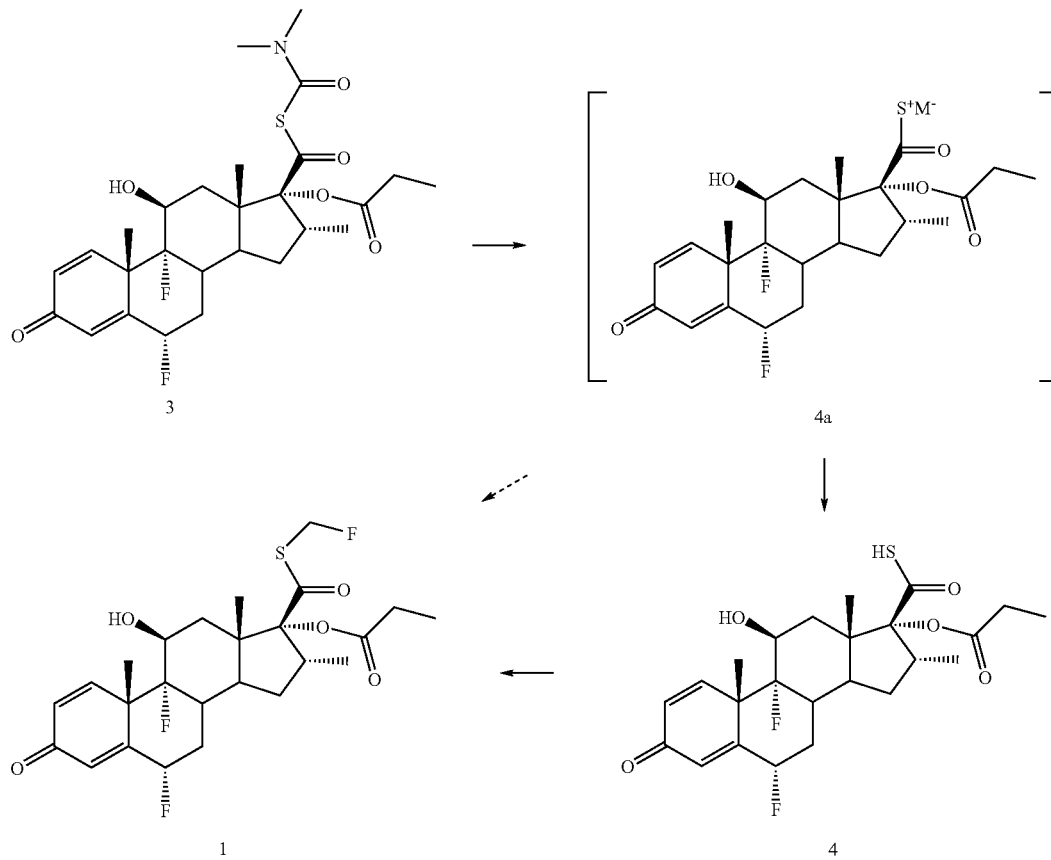

The term "alkali metal carbonate", as used herein, refers to potassium carbonate, sodium carbonate, cesium carbonate and the like. The term "acid", as used herein, refers to reagents capable of donating protons during the course of the reaction. Examples of acids include mineral acids such as HCl, HBr, HI, sulfric acid, phosphoric acid and the like; organic acids such as acetic, formic, trifluoroacetic acid and the like; and sulfonic acids such as para-toluenesulfonic acid and the like.

Further in the process of the present invention for alkylating the compound of formula 4, bromofluoromethane, which is a liquid at below 15° C. is used, as compared to chlorofluoromethane, which is a gas, used in the prior art process of WO 01/62722. The process of the present invention also utilizes lesser molar amounts of bromofluoromethane, as compared to the excessive molar amounts of chlorofluoromethane required in the prior art process. Also, the alkylation with bromofluoromethane requires shorter reaction time.

According to the process of the present invention, in step 'a' of the process, the compound of formula 3 is treated with alkali metal carbonate-alcohol system to obtain the compound of formula 4.

Examples of alkali metal carbonate that can be used include sodium carbonate, potassium carbonate, cesium carbonate and the like. The most preferred alkali metal carbonate is potassium carbonate.

The mole ratio of the alkali metal carbonate to the compound of formula 3 is between the range of 1:1 to 10:1. The preferred mole ratio is 1.5:1.

In the process of the present invention the compound of formula 3 is treated with alkali metal carbonate-alcohol system. The term alcohol, as used herein is an organic compound containing a 'hydroxyl' group. Examples include alkanols, aromatic alcohols, phenols, glycols, diols and the like. Preferably, the alcohol that may be used in the present invention has a boiling point greater than 55° C. under standard conditions of temperature and pressure. In a preferred embodiment the alcohol is an alkanol which may be any straight, branched or cyclic, substituted or unsubstituted, primary, secondary or tertiary alkanol or a mixture thereof. In a more preferred embodiment the alcohol is a linear alkanol containing 1 to 3 carbons. In a still more preferred embodiment the linear alkanol is methanol.

The compound of formula 3 is treated with alkali metal carbonate-alcohol system at temperature between the range of about 0° C. to about 100° C., preferably between the range of about 20° C. to about 30° C.

In a preferred embodiment, the compound of formula 3 is treated with potassium carbonate-methanol system.

In a preferred embodiment of the process of the present invention, the compound of formula 3 is treated with potassium carbonate-methanol system at ambient temperature for about 3 hour to about 10 hours. The reaction mixture is worked up by addition of water, followed by washing with an organic solvent such as toluene. The separated aqueous layer is acidified with an acid such as HCl acid to pH of about 1.5 to about 2 and the precipitated product is isolated.

In step 'b' of the process of the present invention, the compound of formula 4 is alkylated with bromofluoromethane. The compound of formula 4 can be isolated and then treated with bromofluromethane to obtain compound of formula 1. Alternately, it is also possible to directly react the in-situ formed salt of compound of formula 4 with bromofluromethane to obtain the compound of formula 1 in a one pot synthesis.

The mole ratio of bromofluoromethane to the compound of formula 4 may be in the range of about 1:1 to about 10:1. Preferably, the mole ratio of bromofluoromethane to the compound of formula 4, used in the process of the present invention, is about 1.3:1.

The reaction of compound of formula 4 with bromofluoromethane is carried out at a temperature below about 15° C., preferably between the range of about −5° C. to about 0° C. The reaction of compound of formula 4 with bromofluoromethane can be carried out in any polar protic or aprotic solvent. Examples of aprotic solvent are dimethylformamide, dimethylacetamide, dimethylsulfoxide and the like. Protic solvents like alkanols can also be used. Other polar solvents such as ketones, for example, acetone, ethyl methyl ketone, isobutyl methyl ketone and the like or nitriles, for example, acetonitrile can also be used. The preferred solvent for carrying out the reaction of compound of formula 4 with bromofluoromethane is acetone.

The reaction of compound of formula 4 with bromofluoromethane is carried out in presence of a suitable base such as an alkali metal carbonate or alkali metal bicarbonate. The preferred base is potassium carbonate or cesium carbonate, more preferred base is potassium carbonate.

In a preferred embodiment of the process of the present invention, the compound of formula 3 is treated with potassium carbonate-methanol system at ambient temperature for about 3 hour to about 10 hour. The reaction mixture is worked up by addition of water, followed by washing with an organic solvent such as toluene. The separated aqueous layer is acidified with an acid such as HCl acid to pH of about 1.5 to about 2 and the precipitated product is isolated to obtain a compound of formula 4. The compound of formula 4 is reacted with bromofluoromethane in presence of potassium carbonate in acetone at about 0° C. to about −5° C. for a period of about 3 hours to about 10 hours. The reaction is quenched by addition of water and the precipitated product is isolated to obtain a compound of the formula 1.

It is also possible to prepare the compound of formula 1 by the process of the present invention wherein the compound of formula 3 is treated with an alkali metal carbonate-alcohol system to obtain the compound of formula 4a which is not treated with an acid but is converted to compound of formula 1 directly by reaction with bromofluoromethane.

The compound of formula 1 may be purified by treatment with a solvent system comprising one or more organic solvents selected from alcohols, esters, ethers, ketones, amides, nitrites, aliphatic or aromatic hydrocarbons, halogenated hydrocarbons and mixtures thereof. The ratio of the organic solvent to the compound of formula 1 is in the range of about 1:1 to about 50:1.

In a preferred embodiment the compound of formula 1 is purified by treatment with a solvent mixture of methanol: dichloromethane 1:1 v/v.

In the process of the present invention the compound of formula 3 when treated with alkali metal carbonate-alcohol system such as potassium carbonate-methanol, will generate low levels of an ester impurity, such as the methyl ester impurity, a compound of formula 8,

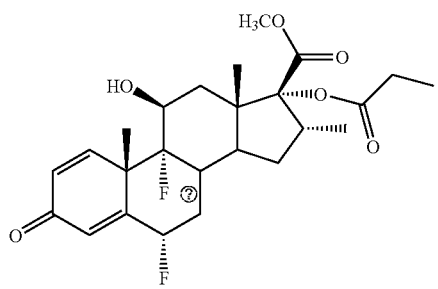

Ⓐ indicates text missing or illegible when filed which can be detected by HPLC.

The compound of formula 3 can be prepared, for example, by reacting 6α,9α-difluoro-11β-hydroxy-16α-methyl-17α-propionyloxy-3-oxoandrosta-1,4-dien-17β-carboxylic acid, a compound of formula 2, with N,N-dimethylthiocarbamoyl chloride in an inert aprotic solvent in the presence of an iodide catalyst and a base. In the prior art process of WO 01/62722 the compound of formula 2 is reacted with N,N-dimethylthiocarbamoyl chloride in 2-butanone and sequentially treated with triethylamine, sodium iodide and water. However, the reaction mixture becomes unstirrable slurry after addition of sodium iodide and water. Whereas, in the process of the present invention it was observed that when the compound of formula 2 is reacted with N,N-dimethylthiocarbamoyl chloride in tetrahydrofuran and sequentially treated with triethylamine and catalytic tetrabutyl ammonium iodide the reaction mixture remains clear.

In a preferred embodiment the compound of formula 3 is prepared by reacting a compound of formula 2 with N,N-dimethylthiocarbamoyl chloride in ether solvent, preferably tetrahydrofuran; in presence of tetrabutylammonium iodide catalyst and an organic base such as triethylamine, preferably at between about 0° C. to about 25° C. Preferably the mole ratio of the iodide catalyst to the compound of formula 2 is 0.1:1.

In another aspect the present invention provides an improved process for the preparation of S-fluoromethyl 6α,9α-difluoro-11β-hydroxy-16α-methyl-17α-propionyloxy-3-oxoandrosta-1,4-diene-17β-carbothioate, a compound of formula 1, comprising (a) reacting 6α,9α-difluoro-11β-hydroxy-16α-methyl-17α-propionyloxy-3-oxo-androsta-1,4-dien-17β-carboxylic acid, a compound of formula 2, with N,N-dimethylthiocarbamoyl chloride in an inert aprotic solvent in the presence of an iodide catalyst and a base to give a compound of formula 3, (b) reacting the compound of formula 3 with a hydrosulfide reagent and bromofluromethane to obtain a compound of formula 1.

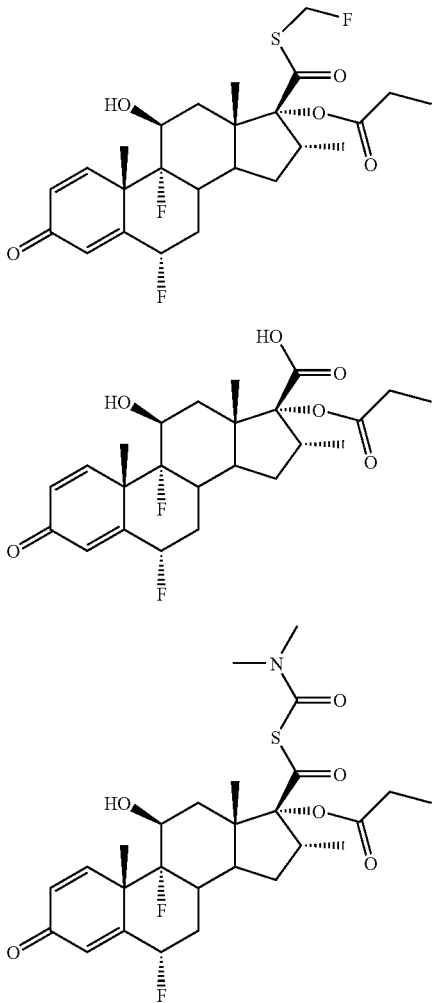

The base selected may be inorganic or organic. Examples of inorganic bases that may be used in the present invention include hydrides, hydroxides, carbonates, or fluorides of alkali or alkaline earth metals. The organic base may be selected from secondary or tertiary amines and quaternary ammonium bases which may be cyclic or acyclic, Preferably, the organic base is selected from hindered acyclic or cyclic tertiary amines and quaternary ammonium bases. In a preferred embodiment, an organic base is used. Particularly preferred organic base is triethylamine.

The iodide catalyst may be an iodide salt selected from alkali metal iodides, alkaline earth metal iodides and quaternary ammonium iodides, the preferred catalyst being quaternary ammonium iodides, most preferably tetrabutylammonium iodide. The mole ratio of the catalyst to 6α,9α-difluoro-11β-hydroxy-16α-methyl-3-oxo-17α-(propionyloxy)androsta-1,4-dien-17β-carboxylic acid, the compound of formula 2 that may be used in the process of the present invention lies in the range of about 0.01:1 to about 0.5:1. The preferred mole ratio of the iodide catalyst:compound of formula 2 is 0.1:1.

The reaction of a compound of formula 2 with N,N-dimethylthiocarbamoyl chloride may be carried out in an inert aprotic solvent such as aliphatic or aromatic hydrocarbons, ethers, esters, nitrites and amides, or mixtures thereof.

The preferred solvents are cyclic or acyclic ethers such as tetrahydrofuran, dioxane, diethyl ether, diisopropyl ether, tertbutyl methyl ether and the like or mixtures thereof; more preferably tetrahydrofuran is used as the solvent. The reaction of a compound of formula 2 with N,N-dimethylthiocarbamoyl chloride may be carried out at temperature ranging from about -10° C. to about 100° C., preferably from about 0° C. to about 25° C.

Preferably the compound of formula 3 is prepared by treating the compound of formula 2 with N,N-dimethylthiocarbamoyl chloride in tetrahydrofuran, in the presence of triethylamine and tetrabutylammonium iodide at room temperature, followed by cooling to about 10–15° C. The reaction mixture is warmed to ambient temperature and stirred for 2–8 hours, preferably for 4 hours. At the end of the reaction, the reaction mixture is treated sequentially with a polar aprotic solvent and water. This polar aprotic solvent may be selected from dimethylformamide, dimethylacetamide and dimethyl sulfoxide and the like; the preferred solvent being dimethylacetamide. The mixture is then cooled to 0° C., stirred and the compound of formula 3 is isolated.

The compound of formula 3 is reacted with a hydrosulfide agent and bromofluoromethane to obtain the compound of formula 1. The hydrosulfide reagent may be selected from hydrated or anhydrous hydrosulfide salts, such as potassium hydrosulfide, sodium hydrosulfide, lithium hydrosulfulfide, quaternary ammonium hydrosulfides and the like. Preferably, sodium hydrosulfide is used in the process of the present invention. The hydrosulfide salt may be taken in a suitable solvent which facilitates nucleophilic substitution, such as dimethylformamide, dimethylacetamide, N-methylpyrrolidin-2-one, dimethylsulfoxide and the like; the preferred solvent being dimethylacetamide.

The mole ratio of bromofluoromethane to the compound of formula 3 may be between the range of about 1:1 to about 5:1. Preferably, the mole ratio of bromofluoromethane to the compound of formula 3, used in the process of the present invention, is 3:1.

In a preferred embodiment of the process of the present invention, the compound of formula 3 is treated with sodium hydrosulfide in dimethylacetamide at low temperature, like 0° C., for about one hour to about 6 hours, preferably for about 2 hours, followed by warming to room temperature and stirring for about one hour to about 5 hours, preferably for about 2 hours. The mixture is then cooled to below 0° C., like -2° C. to -10° C., preferably to about -5° C., and treated with bromofluoromethane. The reaction mixture is stirred further for about half an hour to about 4 hours, preferably for about 1 hour. At the end of the reaction, the mixture is preferably stirred with an oxidizing agent such as aqueous sodium hypochloride, sodium chlorite, hydrogen peroxide, and the like, preferably aqueous hydrogen peroxide, in order to oxidize other sulfide side products that may be formed during the reaction. The solid product is then filtered, washed with water and dried under vacuum to yield the compound of formula 1.

The compound of formula 2, 6α,9α-difluoro-11β-hydroxy-16α-methyl-3-oxo-17α-(propionyloxy)androsta-1,4-diene-17β-carboxylic acid, may be prepared in conventional manner e.g. by oxidation of 6α,9α-difluoro-11β,17α-dihydroxy-16α-methyl-3,20-dione-21-hydroxy-androsta-1,4-diene i.e. flumethasone, followed by reaction with propionyl chloride or propionyl anhydride. The oxidation reaction may be carried out with a suitable oxidizing agent such as periodic acid.

Given below is the schematic representation of a preferred process by which a compound of the formula 2 may be prepared.

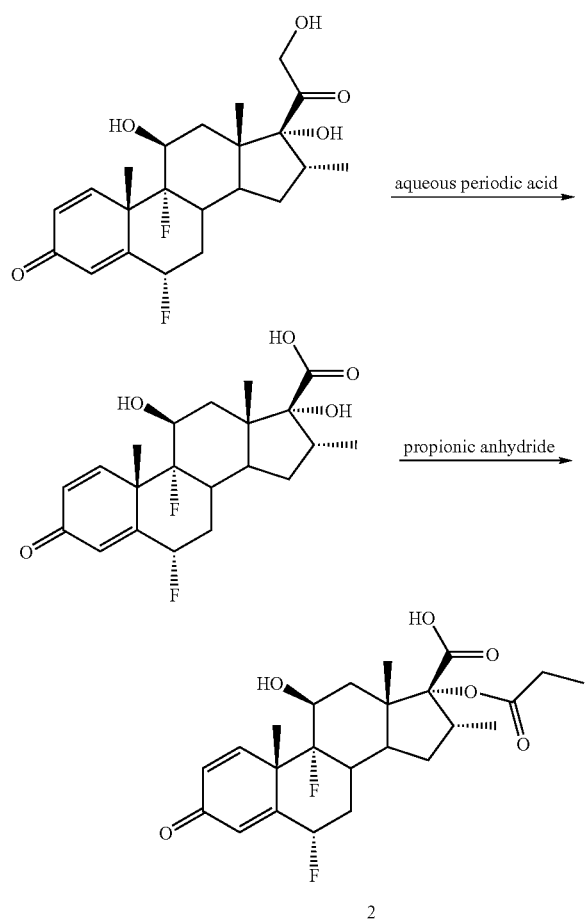

EXAMPLES

Example 1

Preparation of 6α,9α-difluoro-11β,17α-dihydroxy-16α-methyl-3-oxoandrosta-1,4-diene-17β-carboxylic acid A solution of periodic acid (83 g, 0.365 mole) in water (200 ml) is prepared by heating to 50–55° C. and cooling to 30–35° C. This solution is added dropwise to a stirred suspension of flumethasone (100 g, 0.244 mole) in tetrahydrofuran (400 ml) at 0–5° C. After completion of addition the mixture is stirred for further 2 hrs. at 0–5° C. and thereafter quenched by addition of water (600 ml) while maintaining temperature at 5–15° C., then cooled to 0–5° C. and filtered. The product 6α,9α-difluoro-11β,17α-dihydroxy-16α-methyl-3-oxoandrosta-1,4-diene-17β-carboxylic acid is washed with water (~2.0 ltr), and dried at 45–50° C. Yield 92.0 g (95.3%, purity 99.55%).

Example 2

Preparation of 6α,9α-difluoro-11β-hydroxy-16α-methyl-17α-propionyloxy-3-oxoandrosta-1,4-diene-17β-carboxylic acid, a compound of formula 2

To suspension of 6α,9α-difluoro-11β,17α-dihydroxy-16α-methyl-3-oxoandrosta-1,4-diene-17β-carboxylic acid (80 g, 0.202 mole) in acetone (400 ml) at 10–15° C. is added sequentially triethylamine (85 ml, 0.606 mole) and propionic anhydride (78 ml, 0.606 mole). After stirring for 4 hrs. at 25–30° C., diethylamine (42 ml, 0.404 mole) is added dropwise at 10–15° C. and then stirred at ambient temperature for 1 hr. Thereafter the reaction mixture is acidified to pH 1.0–1.5 at 0–5° C. The precipitated product is filtered, washed with water, and dried at 4–45° C., until water content is below 5%. Yield 90 g on dry basis (98.6%, purity>99.5%).

Example 3

Preparation of 17β-[(N,N-dimethylcarbamoyl)thio]carbonyl-6α,9α-difluoro-11β-hydroxy-16α-methyl-17α-propionyloxy-3-oxoandrosta-1,4-diene, a compound of formula 3

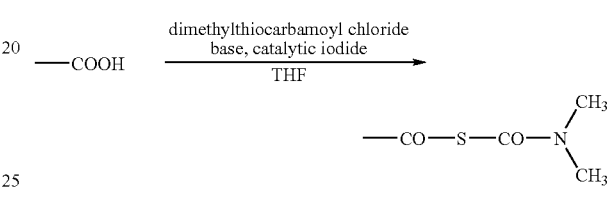

A solution of 6α,9α-difluoro-11β-hydroxy-16α-methyl-17α-propionyloxy-3-oxoandrosta-1,4-diene-17β-carboxylic acid, (50.0 g, 110 mmol) and N,N-dimethylthiocarbamoyl chloride (27.4 g, 222 mmol) in tetrahydrofuran (250 ml) at room temperature is cooled to 10 to 15° C. It is sequentially treated with triethylamine (24.9 g, 244 mmol) and tetrabutylammonium iodide (4.1 g, 11 mmol) at 10–15° C. The reaction mixture is warmed to ambient temperature, stirred for 4 hrs and then treated sequentially with dimethylacetamide (150 ml) and water (1.0 lit). The resultant mixture is cooled to 0° C., stirred for 2 hours, and the product is filtered. The solid obtained is washed with water (230 ml) and dried at 55° C. for 4.0 hours to provide 57.0 g (96.0% yield, purity>98.5%) of 17β-[(N,N-dimethylcarbamoyl)thio]carbonyl-6α,9α-difluoro-11β-hydroxy-16α-methyl-17α-propionyloxy-3-oxoandrosta-1,4-diene.

Example 4

Preparation of 6α,9α-difluoro-11β-hydroxy-16α-methyl-17α-propionyloxy-3-oxoandrosta-1,4-diene-17β-carbothioic acid, a compound of formula 4

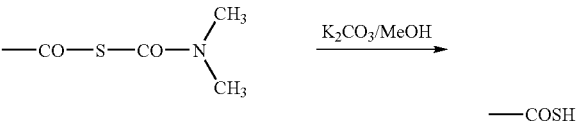

A suspension of 17β-[(N,N-dimethylcarbamoyl)thio]carbonyl-6α,9α-difluoro-11β-hydroxy-16α-methyl-17α-propionyloxy-3-oxoandrosta-1,4-diene (20 g, 0.037 mol.) and potassium carbonate (10.23 g, 0.074 mol.) in methanol (100 ml) is stirred at ambient temperature for 5 hrs under a blanket of nitrogen. Thereafter, water (100 ml) is added to the reaction mixture and the resultant clear solution is washed twice with toluene (40 ml). The aqueous layer containing the product is charcoalized (2 g charcoal) at ambient temperature and then acidified with 2N HCl until pH is 1.5 to 2.0. The precipitated product is filtered, washed with water, and dried at 50–60° C. to obtain 6α,9α-difluoro-11β-hydroxy-16α-methyl-17α-propionyloxy-3-oxoandrosta-1,4-diene-17β-carbothioic acid (5) (yield 17.3 g, moisture content 3.3%, 96.33% on dry basis).

Example 5

Preparation of S-fluoromethyl 6α,9α-difluoro-11β-hydroxy-16α-methyl-17α-propionyloxy-3-oxoandrosta-1,4-diene-17β-carbothioate, compound of formula 1

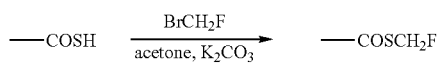

A stirred mixture of 6α,9α-difluoro-11β-hydroxy-16α-methyl-17α-propionyloxy-3-oxo-androsta-1,4-diene-17β-carbothioic acid (5) (4 g, 0.0085 mol)) and anhydrous potassium carbonate (0.82 g, 0.0059 mol.) in acetone (20 ml) under a blanket of nitrogen is cooled to 0 to −5° C. and bromofluoromethane (1.05 g, 0.009 mol.) is added. The mixture is then stirred at 0 to −5° C. for further 5 hrs and then quenched with water (20 ml). The precipitated product is filtered, washed with water (8 ml), and dried to obtain crude product (yield: 3.625 g, moisture content 0.36%, 84.8%, purity 98.11%).

The crude fluticasone obtained as above is dissolved in 68 ml 1-butanol at 117–120° C. to get a clear solution (which may be optionally charcoalized and filtered hot), and then gradually cooled to ambient temperature for crystallization. The crystallized product is filtered. washed with 1-butanol (4 ml). Dried at 55–60° C. to obtain pure fluticasone propionate (Yield 3.0 g, purity 99.24%).

Example 6

Preparation of 6α,9α-difluoro-11β-hydroxy-16α-methyl-17α-propionyloxy-3-oxoandrosta-1,4-diene-17β-carbothioic acid

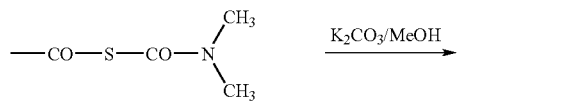

A suspension of 17β-[(N,N-dimethylcarbamoyl)thio]carbonyl-6α,9α-difluoro-11β-hydroxy-16α-methyl-17α-propionyloxy-3-oxoandrosta-1,4-diene (5.2 kg, 9.63 mol), and anhydrous potassium carbonate (2.0 kg, 14.47 mol) in methanol (26 lit) is stirred at ambient temperature for 7 hrs under blanket of nitrogen. Thereafter, water (26 lit) is added to the reaction mixture and the resulting clear solution is washed with toluene (16 lit). The aqueous layer containing product is then acidified with 6N HCl until pH is 1.5 to 2.0. The precipitated product is filtered, washed with water, and dried at 50–60° C. to obtain 6α, 9α-difluoro-11β-hydroxy-16α-methyl-17α-propionyloxy-3-oxoandrosta-1,4-diene-17β-carbothioic acid (yield 4.53 kg, water content 3.71%, theoretical yield 96.6%, purity 99.07%).

Example 7

Preparation of S-fluoromethyl 6α,9α-difluoro-11β-hydroxy-16α-methyl-17α-propionyloxy-3-oxoandrosta-1,4-diene-17β-carbothioate [compound of formula 1, fluticasone propionate]

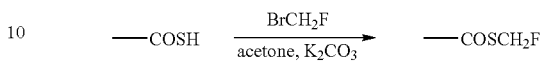

A stirred mixture of 6α,9α-difluoro-11β-hydroxy-16α-methyl-17α-propionyloxy-3-oxoandrosta-1,4-diene-17β-carbothioic acid (25 g, 0.053 mol) and anhydrous potassium carbonate (6.0 g, 0.043 mol) in acetone (125 ml) under a blanket of nitrogen is cooled to 0 to −5° C. and bromofluoromethane (7.53 g, 0.066 mol) is added. The mixture is stirred at 0 to −5° C. for further 5 hrs and then quenched with water (125 ml), stirred for 30 min. The precipitated product is filtered, washed with acetone:water 1:1 mixture (2×40 ml), and dried to obtain crude product (purity: 98.68%).

Purification Using 1-butanol-

The crude fluticasone (10 g) is dissolved in 1-butanol (200 ml) at 115–120° C. Gradually cool to ambient temperature and stirred for 1 hr. The crystallized product is filtered and washed with 1-butanol (10 ml). Dried at 60–62° C. to obtain pure fluticasone propionate (recovery 8.5 g, purity 99.40%).

Purification Using 1-butanol-methylene chloride-

The crude fluticasone (10 g) obtained as above is dissolved in mixture of 1-butanol (110 ml) and methylene chloride (10 ml) under stirring at ambient temperature and charcoalized. Recovered methylene chloride from it under atmospheric pressure.

Gradually cool to 10° C. and stirred for 30 min. The crystallized product is filtered and washed with 1-butanol (10 ml). Dried at 55–60° C. to obtain pure fluticasone propionate (recovery 9.0 g, purity 99.35%).

Example 8

Preparation of Fluticasone Propionate on Kilogram Scale

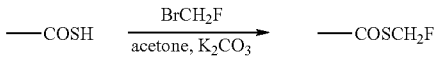

A stirred mixture of 6α,9α-difluoro-11β-hydroxy-16α-methyl-17α-propionyloxy-3-oxoandrosta-1,4-diene-17β-carbothioic acid (4.53 kg, 9.67 mol) and anhydrous potassium carbonate (1.09 kg, 7.89 mol) in acetone (22.6 lit) under a blanket of nitrogen is cooled to 0 to −5° C. Bromofluoromethane (1.40 kg, 12.40 mol) is then introduced, the reaction mixture is stirred at 0 to −5° C. for further 2 hrs and then quenched with water (22.6 lit.), stirred for 60 min. The precipitated product is filtered, washed with water (9 lit), and dried to obtain crude product (Yield 4.66 kg, theoretical yield 96.28%).

Purification:

The fluticasone (4.66 kg) obtained as above is dissolved in mixture of methanol (45 lit) and dichloromethane (45 lit) under stirring at ambient temperature and charcoalized. The methylene chloride is recovered (by distillation) by distillation at atmospheric pressure. The mixture is then gradually cooled to 10° C. and stirred for 60 min. The crystallized product is filtered, washed with methanol (4.5 lit) and dried at 55–60° C. to obtain pure fluticasone propionate (Yield 4.09 kg, overall yield 84.51%, purity 99.37%).

Example 9

One pot preparation of fluticasone propionate from 17β-[(N,N-dimethylcarbamoyl)thio]carbonyl-6α,9α-difluoro-11β-hydroxy-16α-methyl-17α-propionyloxy-3-oxoandrosta-1,4-diene and bromofluromethane using potassium carbonate-methanol system

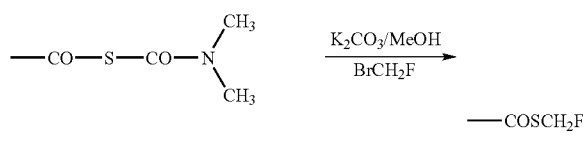

A suspension of 17β[(N,N-dimthylcarbamoyl)thio]carbonyl-6α,9α-difluoro-11β-hydroxy-16α-methyl-17α-propionyloxy-3-oxoandrosta-1,4-diene (5.0 g, 9.2 mmol) and anhydrous potassium carbonate (2.6 g, 18.8 mmol) in methanol (25 ml) is stirred at ambient temperature for 5.5 hrs under blanket of nitrogen. The suspension is cooled to 0 to –5° C. and added bromofluoromethane (2.82 g, 24.95 mmol) and stirred for 7.5 hrs at 0° C. Methanol is recovered under reduced pressure at 50–55° C. and added 50 ml DM water is added to the obtained residue, and stirred at ambient temperature for 40 min. Slurry of the crude product filtered and dried in air oven at 50–60° C. Weight if the crude product: 4.26 g (Yield: 91.85%, purity 96.53%).

Example 10

One pot preparation of fluticasone propionate from 17β-[(N,N-dimethylcarbamoyl)thio]carbonyl-6α,9α-difluoro-11β-hydroxy-16α-methyl-17α-propionyloxy-3-oxoandrosta-1,4-diene and bromofluromethane using hydrosulfide-dimethylacetamide system

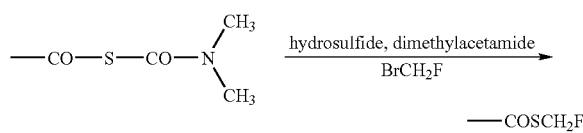

A solution of 17β-[(N,N-dimethylcarbamoyl)thio]carbonyl-6α,9α-difluoro-11β-hydroxy-16α-methyl-17α-propionyloxy-3-oxoandrosta-1,4-diene, compound of formula 3 (20.0 g, 37 mmol) and sodium hydrosulfide hydrate (9.4 g, 113 mmol) in dimethylacetamide (80 ml) at 0° C. is stirred under nitrogen blanketing for 2 hours; warmed to room temperature and again stirred for 2 hours. The mixture is then cooled to –5° C., treated slowly with a solution of bromofluoromethane (12.6 g, 111 mmol) in dimethylacetamide (25 ml), and stirred for 1 hour. A 5% aqueous solution of hydrogen peroxide (40 ml) was added and the mixture stirred for 0.5 hours at ambient temperature (reaction mixture should be positive to starch iodide paper). It is then treated with a solution of sodium bicarbonate (7.5 g) in water (375 ml) at –5° C., stirred for 1 hour, and filtered to provide a solid. The solid is washed with water (250 ml) and dried at 55° C. under vacuum, to provide 20 g of crude compound of formula 1 (purity>97%).

Purification:

The compound of formula 1 obtained above is dissolved in ethyl acetate (0.8 lit.), stirred with 5% aqueous sodium carbonate solution (200 ml), and the mixture is filtered through Hyflo® bed. The aqueous layer is separated out and back extracted with ethyl acetate (200 ml). The combined organic extracts are sequentially washed with water (250 ml), 1.0N hydrochloric acid solution (200 ml), and water (200 ml). The organic layer is dried over anhydrous sodium sulfate, filtered through a micron filter (5 microns) and concentrated under reduced pressure at 40–45° C. to ca. 60 ml. The suspension is refluxed for 30 min, gradually cooled to ambient temperature, stirred for 1 hour and the solid is collected by filtration. The solid obtained is washed with chilled ethyl acetate (30 ml, 10–15° C.) and dried at 45° C. under vacuum to provide 15.5 g (85%) of compound of formula 1 meeting quality requirements as per British Pharmacopoeia.

Example 11

Given below in Table 1 is the result observed by monitoring the reaction by HPLC when 17β-[(N,N-dimethylcarbamoyl)thio]carbonyl-6α,9α-difluoro-11β-hydroxy-16α-methyl-17α-propionyloxy-3-oxoandrosta-1,4-diene, compound of formula 3 is converted to 6α,9α-difluoro-11β-hydroxy-16α-methyl-17α-propionyloxy-3-oxoandrosta-1,4-diene-17β-carbothioic acid, compound of formula 4 in presence of an alkali metal carbonate (2 mole equivalent) at ambient temperature in methanol (5 volumes).

TABLE 1

| | Potassium carbonate (K$_2$CO$_3$) | | | Cesium carbonate (Cs$_2$CO$_3$) | | |
|---|---|---|---|---|---|---|
| Reaction time, hours | Compd. of formula 3* | Compd. of formula 4* | Methyl ester impurity* (Compd. of formula 8) | Compd. of formula 3* | Compd. of formula 4* | Methyl ester impurity* (Compd. of formula 8) |
| 1 | 67.53 | 31.38 | 0.18 | 46.73 | 50.96 | 0.85 |
| 2 | 42.52 | 55.94 | 0.31 | 27.5 | 69.35 | 1.28 |
| 3 | 20.38 | 75.21 | 0.58 | 11.46 | 84.75 | 1.64 |

TABLE 1-continued

| | Potassium carbonate (K$_2$CO$_3$) | | | Cesium carbonate (Cs$_2$CO$_3$) | | |
|---|---|---|---|---|---|---|
| Reaction time, hours | Compd. of formula 3* | Compd. of formula 4* | Methyl ester impurity* (Compd. of formula 8) | Compd. of formula 3* | Compd. of formula 4* | Methyl ester impurity* (Compd. of formula 8) |
| 4 | 3.06 | 94.13 | 0.61 | 1.87 | 93.63 | 2.03 |
| 5 | 0.08 | 94.58 | 0.64 | 1.05 | 94.13 | 2.23 |

*percentages as determined, from relative peak areas in HPLC chromatogram

The invention claimed is:

1. A process for the preparation of S-fluoromethyl 6α,9α-difluoro-11β-hydroxy-16α-methyl-17α-propionyloxy-3-oxoandrosta-1,4-diene-17β-carbothioate, the compound of formula 1, comprising
   (a) treating the compound of formula 3 with alkali metal carbonate-alcohol system to obtain the compound of formula 4;
   (b) reacting the compound of formula 4 with bromofluoromethane to obtain the compound of formula 1,

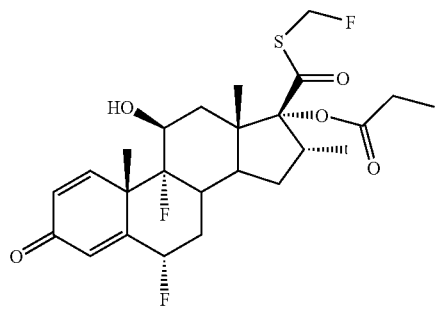

1

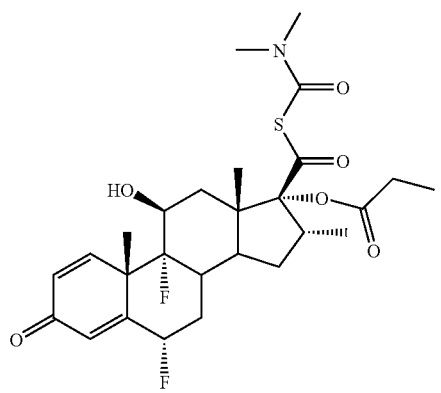

3

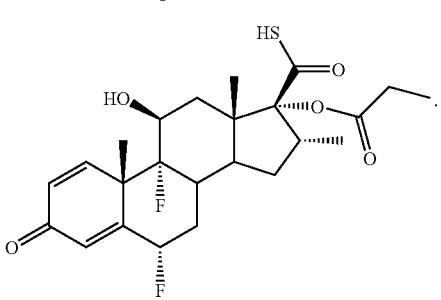

4

2. The process as claimed in claim 1, wherein the alkali metal carbonate is potassium carbonate.

3. The process as claimed in claim 1, wherein the alcohol is an alkanol containing 1 to 3 carbons.

4. The process as claimed in claim 3, wherein the alcohol is a linear alkanol.

5. The process as claimed in claim 4, wherein the linear alkanol is methanol.

6. The process as claimed in claim 1, wherein the mole ratio of alkali metal carbonate to the compound of formula 3 is in the range of 1:1 to 10:1.

7. The process as claimed in claim 6, wherein the mole ratio of alkali metal carbonate to the compound of formula 3 is 1.5:1.

8. The process as claimed in claim 1, wherein the compound of formula 3 is treated with alkali metal carbonate-alcohol system at a temperature in the range of about 0° C. to about 100° C.

9. The process as claimed in claim 8, wherein the compound of formula 3 is treated with alkali metal carbonate-alcohol system at a temperature in the range of about 20° C. to about 30° C.

10. The process as claimed in claim 1, wherein reaction of the compound of formula 4 with bromofluoromethane is carried out at a temperature below about 15° C.

11. The process as claimed in claim 10, wherein reaction of the compound of formula 4 with bromofluoromethane is carried out at a temperature in the range of about −5° C. to about 0° C.

12. The process as claimed in claim 1, wherein the alkali metal carbonate-alcohol system is potassium carbonate-methanol.

13. The process as claimed in claim 1, wherein the mole ratio of bromofluoromethane to the compound of formula 4 is in the range of 1:1 to 10:1.

14. The process as claimed in claim 13, wherein the mole ratio of bromofluoromethane to the compound of formula 4 is 1.3:1.

15. The process as claimed in claim 1, wherein reaction of the compound of formula 4 with bromofluoromethane is carried out in ketone solvent.

16. The process as claimed in claim 15, wherein the ketone solvent is acetone.

17. The process as claimed in claim 1, wherein the compound of formula 3 is prepared by reacting 6α,9α-difluoro-11β-hydroxy-16α-methyl-3-oxo-17α-(propionyloxy) androsta-1,4-dien-17β-carboxylic acid, the compound of formula 2, with N,N-dimethylthiocarbamoyl chloride in an inert aprotic solvent in the presence of an iodide catalyst and a base,

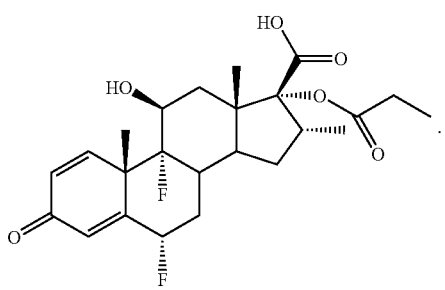

18. The process as claimed in claim 17, wherein the inert aprotic solvent is an ether and the mole ratio of the iodide catalyst to the compound of formula 2 is 0.1:1.

19. The process as claimed in claim 17 wherein the inert aprotic solvent is tetrahydrofuran, the iodide catalyst is tetrabutylammonium iodide, the base is triethylamine and the reaction is carried out at temperature in the range of about 0° C. to about 25° C.

* * * * *